United States Patent
Anderson et al.

(10) Patent No.: US 9,151,761 B2
(45) Date of Patent: Oct. 6, 2015

(54) PREDICTIVE BIOMARKER OF SURVIVAL IN THE TREATMENT OF RENAL CELL CARCINOMA

(75) Inventors: Abraham Antonio Anderson, Sherman Oaks, CA (US); David M. Weinreich, Basking Ridge, NJ (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 14/127,157

(22) PCT Filed: Jun. 28, 2012

(86) PCT No.: PCT/US2012/044673
§ 371 (c)(1),
(2), (4) Date: Jan. 10, 2014

(87) PCT Pub. No.: WO2013/003606
PCT Pub. Date: Jan. 3, 2013

(65) Prior Publication Data
US 2014/0348824 A1    Nov. 27, 2014

Related U.S. Application Data

(60) Provisional application No. 61/502,686, filed on Jun. 29, 2011.

(51) Int. Cl.
G01N 33/53    (2006.01)
G01N 33/574   (2006.01)
A61K 31/17    (2006.01)
A61K 31/435   (2006.01)
A61K 38/18    (2006.01)
A61K 31/44    (2006.01)
A61K 38/02    (2006.01)
A61K 39/395   (2006.01)

(52) U.S. Cl.
CPC .......... *G01N 33/57438* (2013.01); *A61K 31/17* (2013.01); *A61K 31/435* (2013.01); *A61K 31/44* (2013.01); *A61K 38/02* (2013.01); *A61K 38/1891* (2013.01); *A61K 39/39558* (2013.01); *G01N 2333/475* (2013.01); *G01N 2800/52* (2013.01)

(58) Field of Classification Search
None
See application file for complete search history.

(56) References Cited

U.S. PATENT DOCUMENTS

2011/0104161 A1* 5/2011 Burgess et al. ............ 424/133.1

FOREIGN PATENT DOCUMENTS

WO    WO2007/089445    8/2007

OTHER PUBLICATIONS

DePrimo et al (J Traditional Medicine, 2007, 5:32, internet pp. 1-11).*
Motzer et al (J Clinical Oncology, 2006, 24:16-24).*
Rini et al (J Clinical Oncology, 2008, 26:3743-3748).*
Anonymous: "AMG 386, 20060159 Phase 2, RCC 1st Line in Combination with Sorafenib", ClinicalTrials.gov website, Apr. 26, 2007, XP55038336, Retrieved from the Internet on Sep. 17, 2012.
Matsumoto, K. et al., "Prognostic significance of plasma placental growth factor levels in renal cell cancer: An association with clinical characteristics and vascular endothelial growth factor levels," *Anticancer Research* 23(6): 4953-4958, Nov. 1, 2003.
Rini, B., "New strategies in kidney cancer: Therapeutic advances through understanding the molecular basis of response and resistance," *Clinical Cancer Research* 16(5): 1348-1354, Mar. 1, 2010.
Tonini, G. et al., "Predictive factors of response to treatment in patients with metastatic renal cell carcinoma: New evidence," *Expert Review of Anticancer Therapy* 11(6): 921-930, Jun. 1, 2011.

* cited by examiner

*Primary Examiner* — Laura B Goddard
(74) *Attorney, Agent, or Firm* — Raymond M. Doss

(57) ABSTRACT

Methods and compositions are disclosed for predicting and treating the clinical benefit to a human renal cell carcinoma patient prior to their treatment with a VEGFR inhibitor and an Ang2 inhibitor.

22 Claims, 4 Drawing Sheets

PREDICTIVE BIOMARKER OF SURVIVAL IN THE TREATMENT OF RENAL CELL CARCINOMA

CROSS-REFERENCE TO RELATED APPLICATIONS

This application is a national stage application under 35 U.S.C. §371 of International Application No. PCT/US2012/044673, having an international filing date of Jun. 28, 2012; which claims priority to U.S. patent application Ser. No. 61/502,686 filed Jun. 29, 2011 which is incorporated herein by reference.

FIELD OF THE INVENTION

The present invention relates to methods and kits for using placental growth factor (PLGF) as a biomarker for predicting the clinical benefit to renal cell carcinoma patients by treatment with a VEGFR inhibitor and an Ang2 inhibitor.

BACKGROUND OF THE INVENTION

Renal cell carcinoma (RCC) is the most common form of kidney cancer and responsible for approximately 80% of the kidney cancer that occur in adults. RCC represents approximately 5% of all cancer deaths and, at the time of presentation, over 50% of the patients have already developed locally advanced or metastatic disease with 5-year survival rates of less than 20%. Angiogenesis plays a crucial role in RCC tumor progression. Nascent and small tumors can obtain sufficient oxygen and nutrients to sustain their growth by simple diffusion. Beyond a diameter of 1 to 2 mm, however, diffusion cannot provide these elements in the amounts required for further growth. For growth beyond that size, all tumors require a vasculature, whatever their cause, origin, type, age, or location. Thus, tumor growth beyond a diameter of 1 to 2 mm requires angiogenesis. Angiogenesis, accordingly, has been seen as a promising target for developing an effective general treatment for tumors.

Three principal mechanisms play an important part in the activity of angiogenesis inhibitors against tumors: (i) inhibition of the growth of vessels, especially capillaries, into avascular resting tumors, with the result that there is no net tumor growth owing to the balance that is achieved between cell death and proliferation; (ii) prevention of the migration of tumor cells owing to the absence of blood flow to and from tumors; and (iii) inhibition of endothelial cell proliferation, thus avoiding the paracrine growth-stimulating effect exerted on the surrounding tissue by the endothelial cells which normally line the vessels. See R. Connell and J. Beebe, *Exp. Opin. Ther. Patents,* 11:77-114 (2001).

Although many signal transduction systems have been implicated in the regulation of angiogenesis, one of the best-characterized and most endothelial cell-selective systems involves the Tie2 receptor tyrosine kinase (NCBI Reference No. NP_000450.2; referred to as "Tie2" or "Tie2R" (also referred to as "ORK"); murine Tie2 is also referred to as "tek") and its ligands, the angiopoietins (Gale, N. W. and Yancopoulos, G. D., *Genes Dev.* 13:1055-1066 [1999]). There are 4 known angiopoietins; angiopoietin-1 ("Ang1") through angiopoietin-4 ("Ang4"). These angiopoietins are also referred to as "Tie2 ligands."

Yet another important factor associated with tumor angiogenesis is vascular endothelial growth factor (VEGF). VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placental Growth Factor" (PLGF) and VEGF-C. VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

What is needed in the art is a method of predicting which human RCC patients have an increased likelihood of obtaining clinical benefit from treatment with a combination of a VEGFR inhibitor and an Ang2 inhibitor. The present invention provides this as well as other benefits.

SUMMARY OF THE INVENTION

In one aspect the present invention provides a method of predicting human renal cell carcinoma (RCC) patients having an increased likelihood of obtaining clinical benefit from treatment with a therapeutically effective amount of a VEGFR inhibitor and an Ang2 inhibitor. The method includes comparing a patient's PLGF concentration with a PLGF concentration parameter which serves as a reference measurement. If a patient's PLGF concentration is lower than the PLGF concentration parameter then the patient has a statistically increased likelihood of clinical benefit from the Ang2 inhibitor and VEGF inhibitor combination. The patient can then be treated with a therapeutically effective amount of the VEGFR inhibitor and Ang2 inhibitor.

In some embodiments the Ang2 inhibitor is AMG 386 or H4L4. In some embodiments, the VEGFR inhibitor is sorafenib or fluoro-sorafenib. In some embodiments the Ang2 inhibitory activity and the VEGFR inhibitory activity are provided by the same molecule such as fluoro-sorafenib. The Ang2 inhibitor can also be a dual Ang2 and Ang1 inhibitor. The PLGF concentration parameter can be the median or mean serum PLGF concentration of the RCC patients from which PLGF concentration parameter is determined. The patient PLGF concentration can be determined from serum, plasma, or urine. In some embodiments the Ang2 inhibitor is a binding polypeptide which can be, for example, an anti-Ang2 antibody, a soluble Tie2-Fc fusion polypeptide, or an anti-Tie2 antibody. In some embodiments, a bispecific binding polypeptide is an anti-VEGFR and anti-Ang2 binding polypeptide.

BRIEF DESCRIPTION OF THE DRAWINGS

FIG. 1 shows all subjects: data from 123 patients (62 above, 61 below) yielded a Cox proportional hazard ratio (HR) of 1.92 (95% CI (confidence interval): [1.27, 2.92], p=0.00217) and a 169 day difference in median survival;

FIG. 2 shows patients administered 10 mg/kg AMG 386: data from 43 patients (18 above, 25 below) yielded a HR of 2.76 (95% CI: [1.30, 5.87], p=0.00834) and a 284 day difference in median survival;

FIG. 3 shows patients administered 3 mg/kg AMG 386: data from 39 patients (21 above, 18 below) yielded a HR of 3.51 (95% CI: [1.49, 8.25], p=0.00405) and a 221 day difference in median survival;

FIG. 4 showed patients administered sorafenib only: data from 41 patients (23 above, 18 below) yielded a HR of 0.83 (95% CI: [0.42, 1.65], p=0.59) and a 1 day difference in median survival.

Figure 1:
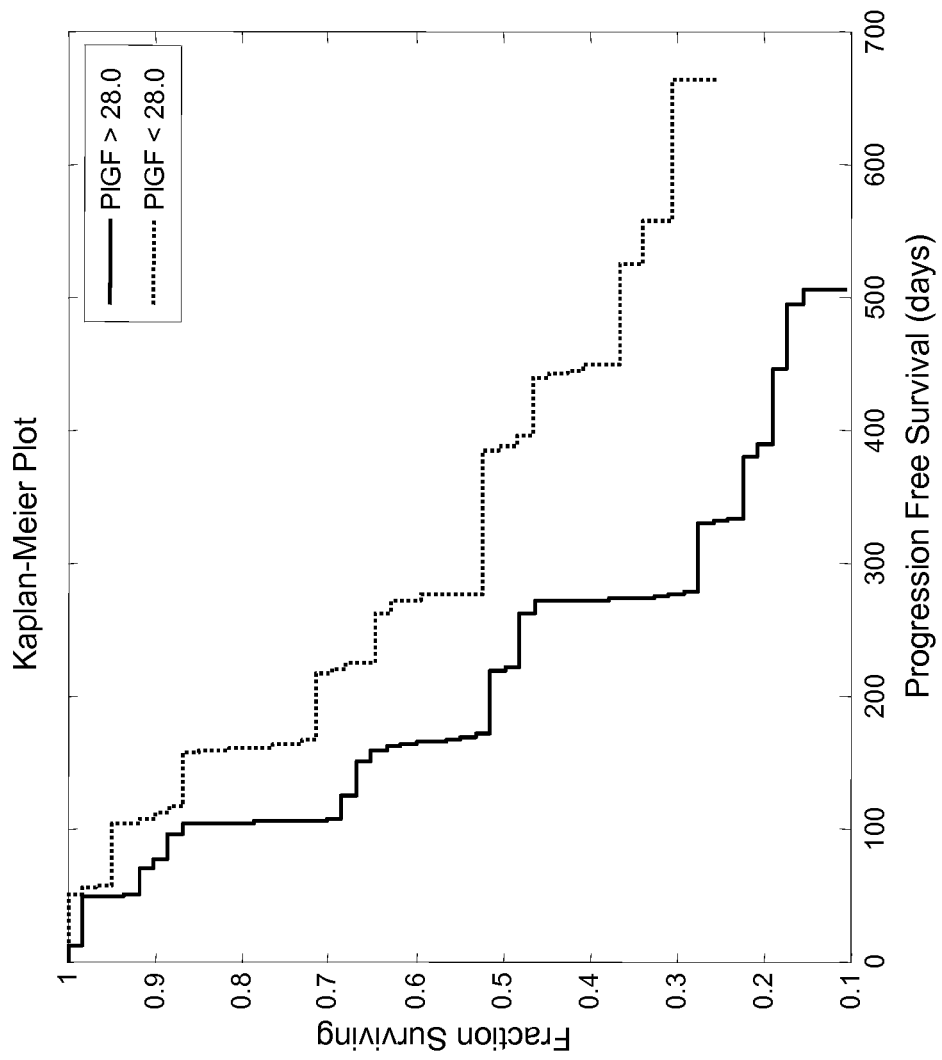
FIGS. 1-4 are Kaplan-Meier plots showing progression free survival differences between subjects with patient PLGF concentrations above and below the median PLGF concentration parameter (28 pg/mL). 123 patients total with 43 patients administered AMG 386 at 10 mg/kg, 39 patients at 3 mg/kg, and 41 patients at 0 mg/kg. All patients were also dosed with 400 mg sorafenib orally, twice a day.
Figure 2:
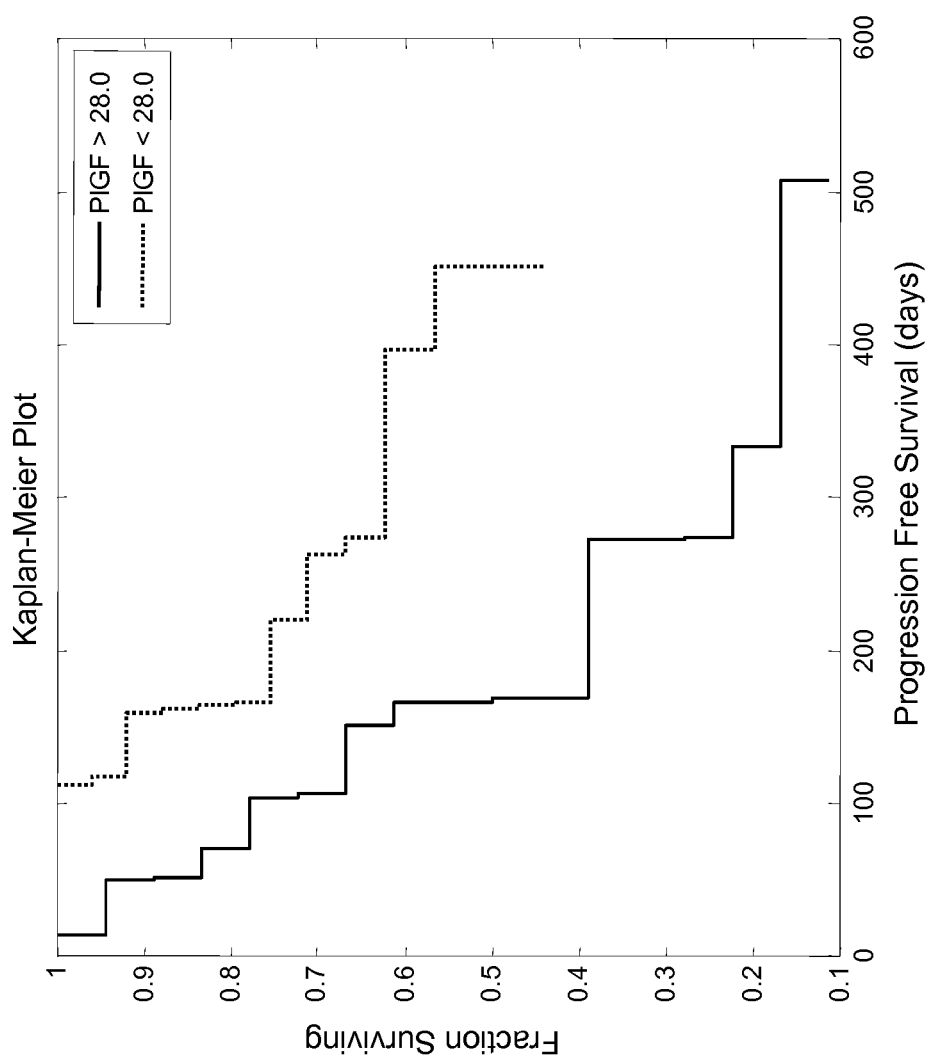
Figure 3:
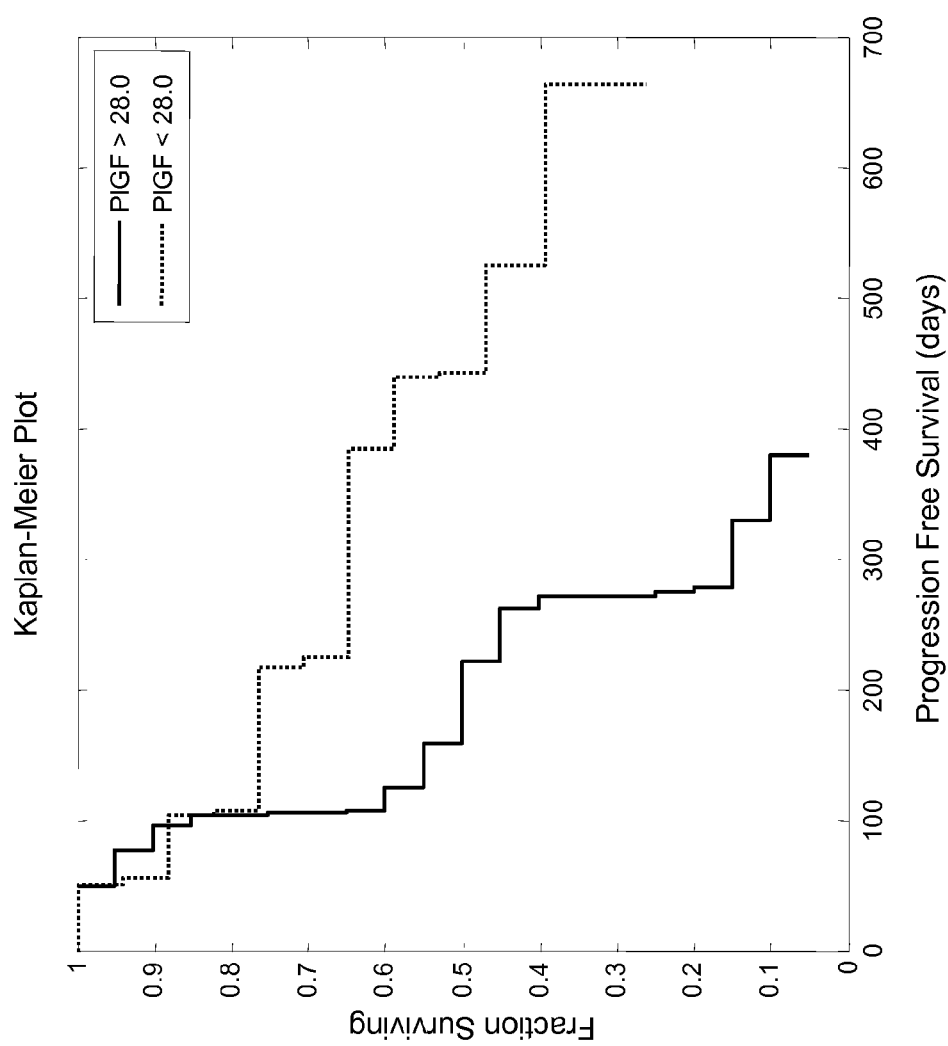

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

The term "Ang2" or "human Ang2" refers to the polypeptide also called angiopoietin 2 set forth, for example, in FIG. 6 (SEQ ID NO: 6) of U.S. Pat. No. 6,166,185 ("Tie2 ligand-2") (see also, National Center for Biotechnology Information (NCBI) Accession No. AAI26203) as well as related native (i.e., wild-type) polypeptides such as allelic variants or mature forms of the polypeptide (absent the signal peptide), or splice variants (isoforms).

The term "Ang1" or "human Ang1" refers to the polypeptide human angiopoietin 1, a ligand of the human Tie2 receptor. An "Ang1 inhibitor" refers to an Ang1-specific binding agent that specifically binds to human Ang1 and/or human Tie2 thereby inhibiting specific binding of human Ang1 to the human Tie2 receptor.

The term "Ang2 inhibitor" refers to an Ang2-specific binding agent and/or a Tie2-specific binding agent that specifically binds to human Ang2 and/or human Tie2, respectively, thereby inhibiting binding of human Ang2 to the human Tie2 receptor and resulting in a statistically significant decrease in angiogenesis, as measured by at least one functional assay of angiogenesis such as, but not limited to, tumor endothelial cell proliferation or the corneal micropocket assay (See, Oliner et al. Cancer Cell 6:507-516, 2004). See also, U.S. Pat. Nos. 5,712,291 and 5,871,723. A corneal micropocket assay can be used to quantify the inhibition of angiogenesis. In this assay, agents to be tested for angiogenic activity are absorbed into a nylon membrane, which is implanted into micropockets created in the corneal epithelium of anesthetized mice or rats. Vascularization is measured as the number and extent of vessel ingrowth from the vascularized corneal limbus into the normally avascular cornea. See, U.S. Pat. No. 6,248,327 which describes planar migration and corneal pocket assays. In certain embodiments, the Ang2 inhibitor is an antibody, avimer (Nature Biotechnology 23, 1556-1561 (2005)), peptibody (Fc-peptide fusion protein; see, WO 00/24782), Fc-soluble Tie2 receptor fusion (i.e., a "Tie2 trap"), or small molecule Ang2 inhibitor.

The term "Ang2-specific binding agent" refers to a molecule that specifically binds to Ang2 and inhibits its binding with Tie2 resulting in a statistically significant decrease in angiogenesis.

The term "antibody" includes reference to isolated forms of both glycosylated and non-glycosylated immunoglobulins of any isotype or subclass, including any combination of: 1) human (e.g., CDR-grafted), humanized, and chimeric antibodies, and, 2) monospecific or multi-specific antibodies, monoclonal, polyclonal, or single chain (scFv) antibodies, irrespective of whether such antibodies are produced, in whole or in part, via immunization, through recombinant technology, by way of in vitro synthetic means, or otherwise. Thus, the term "antibody" is inclusive of those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody (e.g., from a transfectoma), (c) antibodies isolated from a recombinant, combinatorial antibody library, and (d) antibodies prepared, expressed, created or isolated by any other means that involve splicing of immunoglobulin gene sequences to other DNA sequences. In some embodiments the antibodies of the present invention are monoclonal antibodies, such as humanized or fully-human monoclonal antibodies. Typically, antibodies of the present invention will be IgG1 or IgG2 subclass antibodies. The antibody may bind human Ang2 or human Tie2 with a Kd of less than about 10 nM, 5 nM, 1 nM, or 500 pM.

The term "bispecific molecule" is intended to include any agent, e.g., a protein, peptide, or protein or peptide complex, which has at least two different binding specificities. For example, the molecule may specifically bind to two distinct epitopes of the same protein or with two distinct proteins. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al (1993) Proc. Natl. Acad. Sci. USA 90:6444-6448; Poljak, R. J., et al. (1994) Structure 2:1121-1123).

The term "multispecific molecule" or "heterospecific molecule" is intended to include any agent, e.g., a protein, peptide, or protein or peptide complex, which has two or more different binding specificities. Accordingly, the invention includes, but is not limited to, bispecific, trispecific, tetraspecific, and other multispecific molecules.

The term "binding polypeptide" refers to a molecule that comprises a polypeptide wherein the polypeptide specifically binds to a target. Exemplary binding polypeptides include: antibodies, peptibodies, avimers, Fc-soluble receptor fusion ligand trap (e.g., an Fc-soluble Tie2 fusion), CovX-bodies (see, WO 2008/056346), or specifically binding peptides (such as those obtained from screening a peptide library). A binding polypeptide of the present invention includes those that bind to a single epitope as well as multispecific binding polypeptides that bind to two epitopes (bispecific), three (trispecific), four (tetraspecific), or more epitopes.

As used herein, the term "clinical benefit" in the context of treating human RCC refers to a statistically significant decrease in at least one of: the rate of tumor growth, a cessation of tumor growth, or in a reduction in the size, mass, metabolic activity, or volume of the tumor, as measured by standard criteria such as, but not limited to, the Response Evaluation Criteria for Solid Tumors (RECIST), or a statistically significant increase in survival (PFS and/or OS) relative to treatment with a control.

The terms "effective amount" or "therapeutically effective amount" when used in relation to Ang2 inhibitor administered in combination with a VEGFR inhibitor refers to an amount that is determined to provide a statistically significant inhibition (i.e., in size, mass, metabolic activity, or volume) of renal cell carcinoma (RCC) progression in a human RCC cancer patient population of statistically significant size relative to a control. Those of skill will recognize that the effective amount is determined from a patient population and therefore an individual patient may or may not obtain clinical benefit from a therapeutically effective amount but that a statistically significant number of patients in the relevant patient population will obtain clinical benefit.

The term "Fc" in the context of an antibody or peptibody of the present invention is typically fully human Fc, and may be any of the immunoglobulins, although IgG1 and IgG2 are preferred. However, Fc molecules that are partially human, or obtained from non-human species are also included herein.

The term "Fc-peptide fusion" refers to a peptide that is covalently bonded, directly or indirectly, to an Fc. Exemplary Fc-peptide fusion molecules include a peptibody such as those disclosed in WO 03/057134, incorporated herein by reference, as well as an Fc covalently bonded, directly or indirectly, to an Ang2 specific binding fragment of the Tie2 receptor (i.e., a "Tie2 trap").

The term "humanized antibody" refers to an antibody in which substantially all of the constant region is derived from a human, while all or part of one or more variable regions is derived from another species, for example a mouse.

The term "human antibody" refers to an antibody in which both the constant regions and the framework consist of fully or substantially human sequences such that the human antibody elicits substantially no immunogenic reaction against itself when administered to a human host and preferably, no detectable immunogenic reaction.

The term "increased likelihood" or "increased likelihood of obtaining clinical benefit" means a statistically significant probability of obtaining clinical benefit by a group of treated individuals after a specified treatment relative to a control group. Exemplary statistical tests include, but are not limited to, the Cox proportional hazards test of PFS or OS (yielding a p-value of equal to or less than 0.05).

The term "monoclonal antibody" or "monoclonal antibody composition" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The term "monoclonal" is not limited to any particular method for making an antibody.

The term "overall survival" or "OS" refers to the percentage of patients in a study who have survived for a defined period of time.

The terms "peptide," "polypeptide," or "protein" are used interchangeably throughout and refer to a molecule comprising two or more amino acid residues joined to each other by peptide bonds. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

The term "peptibody" refers to a specific binding agent that is a molecule comprising an antibody Fc domain attached to at least one peptide. The production of peptibodies is generally described in PCT publication WO 00/24782, published May 4, 2000, incorporated herein by reference. Exemplary peptides may be generated by any of the methods set forth therein, such as carried in a peptide library (e.g., a phage display library), generated by chemical synthesis, derived by digestion of proteins, or generated using recombinant DNA techniques.

The term "PLGF" or "Placental Growth Factor" refers to human placental growth factor, a member of the VEGF family of growth factors and a specific ligand of VEGFR-1. PLGF in relation to this invention is meant to include in the four known isoforms, PLGF-1, PLGF-2, PLGF-3 and PLGF-4. See, NCBI Accession No. NP 002623.

The term "PLGF concentration parameter" refers to a PLGF concentration to which a patient PLGF concentration is compared.

The term "patient PLGF concentration" refers to the concentration of placental growth factor (PLGF) in a human renal cell carcinoma (RCC) patient. The concentration can be measured in tissue or fluids (including, but not limited to, plasma, serum, or urine).

The term "predictive" or "predicting" in the context of a biomarker, such as PLGF, means that the biomarker provides a means of identifying, directly or indirectly, an increased likelihood of a patient obtaining clinical benefit (PFS and/or OS) upon therapeutic treatment, such as treatment with a therapeutically effective amount of a VEGFR inhibitor and an Ang2 inhibitor. Thus, in this context the present invention provides a means of "identifying" or "determining" an RCC patient having an increased likelihood of clinical benefit prior to being administered a therapeutically effective amount of a VEGFR inhibitor and an Ang2 inhibitor of the invention. Conversely, the term can also be applied to situations in which the biomarker provides a means of predicting, directly or indirectly, patients who are statistically likely to obtain less clinical benefit from such treatment relative to a control.

The term "progression free survival" or "PFS" refers to the time interval from the start of treatment to disease progression. It is a measure of the clinical benefit from therapy.

The term "prognostic" in the context of a biomarker means that the biomarker identifies an increased likelihood of a patient obtaining clinical benefit regardless of treatment.

The term "renal cell carcinoma" or "RCC" or "advanced renal cell carcinoma" or "advanced RCC" refers to human kidney cancer classified as being of at least one of the following histologies: clear cell carcinoma, papillary renal carcinoma (type 1 or type 2), chromophobe renal carcinoma, oncocytoma. Typically, the RCC is at least a clear cell carcinoma but RCC patients collectively may exhibit 2, 3, or all 4 histologies.

The term "specifically binds" refers to the ability of a specific binding agent of the present invention (such as an Ang2-specific binding agent, a Tie2-specific binding agent, or an VEGFR-specific binding agent), under specific binding conditions, to bind a target molecule such that its affinity is at least 10 times as great, but optionally 50 times as great, 100, 250 or 500 times as great, or even at least 1000 times as great as the average affinity of the same specific binding agent to a large collection of random peptides or polypeptides. A specific binding agent has a "binding specificity" for its cognate target or, if there are multiple binding specificities (multispecific), to its cognate targets. A specific binding agent need not bind exclusively to a single target molecule but may specifically bind to a non-target molecule due to similarity in structural conformation between the target and non-target (e.g., paralogs or orthologs). Those of skill will recognize that specific binding to a molecule having the same function in a different species of animal (i.e., ortholog) or to a molecule having a substantially similar epitope as the target molecule (e.g., a paralog) is within the scope of the term "specific binding" which is determined relative to a statistically valid sampling of unique non-targets (e.g., random polypeptides). Thus, a specific binding agent of the invention may specifically bind to more than one distinct species of target molecule. Solid-phase ELISA immunoassays can be used to determine specific binding. Generally, specific binding proceeds with an association constant of at least about $1\times10^7$ $M^{-1}$, and often at least $1\times10^8 M^{-1}$, $1\times10^9$ $M^{-1}$, or, $1\times10^{10}$ $M^{-1}$.

The term "Tie2-specific binding agent" refers to a molecule that specifically binds to human Tie2 and inhibits its binding with Ang2 and/or inhibits human Tie2 signal transduction resulting in a statistically significant decrease in angiogenesis, as measured by at least one functional assay of angiogenesis such as tumor endothelial cell proliferation or the corneal micropocket assay (Oliner et al. Cancer Cell 6:507-516, 2004). See also, U.S. Pat. Nos. 5,712,291 and 5,871,723 (both incorporated herein by reference). In certain embodiments, the Tie2 inhibitor is an antibody, avimer (Nature Biotechnology 23, 1556-1561 (2005)), peptibody, or small molecule Ang2 inhibitor.

The term "VEGFR" refers to human vascular endothelial factor receptors (VEGFR) including VEGFR-1, VEGFR-2, and VEGFR-3.

The term "VEGFR inhibitor" refers to a molecule that inhibits the interaction between VEGF, the native, endogenous ligand of human vascular endothelial growth factor receptor (VEGFR), with a VEGFR. Generally, a VEGFR inhibitor will interfere with signaling between at least VEGFR-2 (also known as KDR) and at least one native ligand VEGF (vascular endothelial growth factor) so as to inhibit angiogenesis. The VEGFR inhibitors of the present invention include sorafenib and fluoro-sorafenib (regorafanib).

PLGF Concentration Parameter

The PLGF (placental growth factor) concentration parameter provides a reference value to which a patient PLGF concentration can be compared. An RCC patient(s) selected for treatment by the method of the invention has a PLGF concentration ("patient PLGF concentration") lower than the PLGF concentration parameter. The PLGF concentration parameter is a PLGF concentration determined from a plurality of RCC patients. From the resulting distribution of PLGF concentration values a PLGF concentration parameter is calculated. The RCC patients who are assessed to determine the PLGF concentration generally have their PLGF concentration determined prior to treatment with a combination of the VEGFR inhibitor and Ang2 inhibitor, or after sufficient time has transpired that the PLGF concentration values obtained from the RCC patients are not significantly affected by the combination treatment or other treatment (i.e., after sufficient washout). For example, the PLGF concentration can be measured in RCC patients and used to determine the PLGF concentration parameter if at least 15, 20, 30, 40, 50, 60, or 75 days have transpired since having been administered an Ang2 inhibitor and/or a VEGFR inhibitor for treatment of cancer or after other treatment that has substantially affected the PLGF concentration.

The number of RCC patients employed in determining the PLGF concentration parameter can vary but is generally a sufficient number to obtain a statistically meaningful value. In some embodiments, the PLGF concentration parameter is a value obtained from a statistical sampling of at least 10, 20, 30, 40, 50, 75, 100, 200, 300, 500, or 1000 RCC patients. RCC patients may have a statistically proportional representation of RCC histologies but can also be chosen such that at least 75%, 80%, 85%, 90%, 95%, or 100% of the patients have clear cell carcinoma.

The particular biological sample from which the PLGF concentration parameter can be determined in a wide variety of ways per the desired requirements. In some embodiments, the PLGF concentration is determined from whole blood of the RCC patients. In other embodiments the PLGF concentration parameter is determined from components of whole blood (such as from serum or plasma), or from urine. Methods for determining PLGF concentration from serum, plasma, or urine are known in the art. Serum, plasma, and urine PLGF concentrations can be analyzed, for example, by sandwich enzyme-linked immunosorbent assay (ELISA) and by an electrochemiluminescent multiplexed sandwich immunoassay (Meso-Scale Discovery [MSD], Gaithersburg, Md.). See also, for example, Quantikine® human PLGF immunoassay which can be used to assay PLGF concentration in serum, plasma, and/or urine. Those of skill in the art will recognize that the specific method of determining the PLGF concentration parameter should provide a value of sufficient accuracy and precision to allow a statistically meaningful comparison to the patient PLGF concentration. Furthermore, the skilled practitioner will recognize that the PLGF concentrations obtained from different methods or from different tissue biological samples (e.g., plasma and serum) can be used but the values will generally be normalized relative to each other so that the values can all be brought to a common scale.

The value of the PLGF concentration parameter that is determined will generally vary between patient populations selected for testing. Thus, for example, in some embodiments the value of the PLGF concentration parameter when determined from human serum from a statistical sampling of RCC patients (and as determined by electrochemiluminescent multiplexed sandwich immunoassay (Meso-Scale Discovery [MSD], Gaithersburg, Md.)) generally ranges from about 22 pg/ml to about 40 pg/ml. Thus, in some embodiments the PLGF concentration parameter as determined from human serum can have a value (expressed in pg/ml) of: 22, 23, 24, 25, 26, 27, 28, 29, 30, 31, 32, 33, 34, 35, 36, 37, 38, 39, or 40.

In some embodiments, the mean (average) value of PLGF concentration from the RCC patients is used for determining a PLGF concentration parameter. In other embodiments, the PLGF concentration parameter is within one standard deviation of the mean PLGF concentration of the RCC patients; often the value is the median PLGF concentration. As desired, more stringent values can be selected. Thus, in some embodiments in which clinical benefit is being determined the PLGF concentration parameter is the value of the $25^{th}$, $30^{th}$, $35^{th}$, $40^{th}$, $45^{th}$, $50^{th}$, $55^{th}$, $60^{th}$, $65^{th}$, $70^{th}$, $75^{th}$, $80^{th}$, $85^{th}$ or $90^{th}$ percentile in the distribution. Thus, in some embodiments the clinician may desire to exclude the top $10^{th}$ percentile (i.e., the $90^{th}$ percentile) from treatment with the combination therapy of the present invention.

Patient PLGF Concentration

The patient PLGF concentration is obtained for the RCC patient for whom treatment with a therapeutically effective dose of a VEGFR inhibitor and an Ang2 inhibitor is being considered. Typically, as is the case for the PLGF concentration parameter, the measurement of the patient PLGF concentration is determined prior to treatment with a VEGFR inhibitor and/or an Ang2 inhibitor so as to obtain a value not altered by one or both agents. However, measurement of the patient PLGF concentration subsequent to treatment with one or both agents if sufficient time has transpired to substantially reduce any affect of one or both of the agents, or of any other agent, on PLGF concentration levels. Thus, if treatment with one or both agents has taken place the patient PLGF concentration can be measured following cessation of treatment with the agent or agents significantly affecting the patients PLGF concentration. For example, the patient PLGF concentration can be measured after 1, 2, 3, 4, 5, 6, 7, 8 weeks cessation of treatment.

The patient PLGF concentration can be measured per the specific methods utilized for measuring the PLGF concentration parameter. Conveniently, the method utilized will be the same for both to ensure better correlation of measured values. Thus, for example, if the PLGF concentration parameter is determined from serum, plasma, or urine then the patient PLGF concentration will conveniently also be measured from serum, plasma, or urine, respectively. Likewise, the specific assay method of measurement will generally also be substantially identical to minimize discrepancies. However, different biological samples and/or assay methods can also be utilized for determining the PLGF concentration parameter and/or the patient PLGF concentration although values thereby obtained will typically be normalized relative to bring each value to a common scale.

Clinical Benefit

The present invention provides means for predicting whether an RCC patient has an increased likelihood of obtaining clinical benefit from a therapeutically effective amount of a VEGFR inhibitor and an Ang2 inhibitor relative to control RCC patients receiving the VEGFR inhibitor alone. One can therefore stratify RCC patients on the basis of the statistical likelihood of responding favorably to this therapeutic combination. The method of the invention comprises comparing the reference PLGF concentration value (the "PLGF concentration parameter") with the PLGF concentration of a human RCC patient (the "patient PLGF concentration"). RCC patients having a patient PLGF concentration lower than the PLGF concentration parameter are predicted to have an increased likelihood of receiving clinical benefit from treatment with a therapeutically effective amount of a VEGFR inhibitor and an Ang2 inhibitor relative to treatment with the VEGFR inhibitor alone.

Those of skill will recognize that RCC patients having a patient PLGF concentration lower than the PLGF concentration parameter can be identified indirectly as well as directly. Thus, by identifying those RCC patients from a group of RCC patients who have a higher patient PLGF concentration than the PLGF concentration parameter one implicitly also identifies those that have a patient PLGF concentration equal to or lower than the PLGF concentration parameter. Likewise, one can identify RCC patients with a patient PLGF concentration higher than the PLGF concentration parameter by identifying the RCC patients in a group of RCC patients by a similar implicit process. Thus, the method of the invention extends to identification of both groups, one directly and one indirectly or implicitly.

Ang2 Inhibitors

The Ang2 inhibitors of the present invention, which are administered in combination with at least one VEGFR inhibitor of the invention, can be small molecules (less than about 1000 daltons) or large molecules (polypeptides of greater than about 1000 daltons). Some exemplary Ang2 inhibitors include AMG 386 (2XCon4C) (Amgen Inc., see U.S. Pat. No. 7,723,499), H4L4 (Amgen Inc.; see U.S. Ser. No. 12/378, 993), CVX-060 (CovX/Pfizer), MEDI3617 (MedImmune/AstraZeneca), DX-2240 (Dyax/Sanofi-Aventis), REGN910 (Regeneron/Sanofi-Aventis), CGI-1842 (CGI Pharmaceuticals), LC06 (Roche), CGEN-25017 (Compugen), RG7594 (Roche), CVX-241 (CovX/Pfizer), LP-590 (Locus Pharmaceuticals), CEP-11981 (Cephalon/Sanofi-Aventis), MGCD265 (Methylgene), regorafenib (Bayer), or CrossMab (Roche).

In some embodiments, the Ang2 inhibitor and the VEGFR inhibitor are functional moieties located on the same multi-specific molecule such as, but not limited to, fluoro-sorafenib (regorafenib; Bayer). Thus, in some embodiments the Ang2 inhibitors have dual Ang2 and VEGFR inhibitory function (a "dual Ang2 and VEGFR inhibitor"). In some embodiments, the Ang2 inhibitor is at least bispecific comprising an Ang2 inhibitor and a human DLL4 (delta like ligand 4) inhibitor (a "dual Ang2 and DLL4 inhibitor"). In some embodiments, the Ang2 inhibitor also inhibits Ang1 binding to the Tie2 receptor (a "dual Ang2 and Ang1 inhibitor"). The Ang2 inhibitors are inclusive of large molecules such as a peptide, peptibody, antibody, antibody binding fragment such as a F(ab) or F(ab')2 fragment, an Fc-Tie2 extracellular domain (ECD) fusion protein (a "Tie2 trap"), and small molecules, or combinations thereof. In some embodiments, the dual Ang2 and Ang1 inhibitor is AMG 386 (Amgen Inc.) or H4L4 (Amgen Inc.). In some embodiments, the VEGFR inhibitor is at least bispecific, for example a dual VEGFR and DLL4 inhibitor. Methods for linking small or large molecule Ang2 inhibitors with other specific binding agents, such as a VEGFR inhibitor of the invention, are known in the art. Thus, for example, bispecific antibodies which act as dual VEGFR and Ang2 inhibitors of the invention can be made using known techniques.

In some embodiments, the Ang2 inhibitor is a binding polypeptide. Binding polypeptides may be produced by methods known to those of skill in the art such as by the modification of whole antibodies, or synthesized de novo using recombinant DNA technologies or peptide synthesis. Human or humanized antibodies or antigen binding regions can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743.

It is possible to produce transgenic animals (e.g. mice) that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germline mutant mice will result in the production of human antibodies upon antigen challenge. See, e.g., Jakobovits et al., Proc. Natl. Acad. Sci USA, 90: 2551 (1993); Jakobovits et al., Nature, 362: 255 (1993); Bruggermann et al., Year in Immunol., 20 7: 33 (1993). Commercially accessible antibodies produced from transgenic mice strains such as XenoMouse® have been described; see, Green et al. Nature Genetics 7:13-21 (1994).

A nucleic acid encoding all or part of the binding polypeptide of the invention can be directly synthesized by methods of in vitro oligonucleotide synthesis known in the art. Alternatively, smaller fragments can be synthesized and joined to form a larger fragment using recombinant methods known in the art. Antibody binding regions, such as for Fab or F(ab')$_2$, may be prepared by cleavage of the intact protein, e.g. by protease or chemical cleavage. Alternatively, a truncated gene can be designed.

To express the antibodies or antigen binding regions thereof, DNAs (deoxyribonucleic acid) encoding partial or full-length light and heavy chains, can be obtained by standard molecular biology techniques (e.g., PCR (polymerase chain reaction) amplification, site directed mutagenesis) and can be inserted into expression vectors such that the genes are operatively linked to transcriptional and translational regulatory sequences. Nucleic acids encoding an antibody or antigen binding region of the invention can be cloned into a suitable expression vector and expressed in a suitable host. Suitable systems for expression can be determined by those skilled in the art.

Nucleic acids comprising polynucleotides of the present invention can be used in transfection of a suitable mammalian or nonmammalian host cells. In some embodiments, for expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE (diethylaminoethyl)-dextran transfection and the like. Although it is theoretically possible to express the antibodies of the invention in either prokaryotic or eukaryotic host cells, expression of antibodies in eukaryotic cells, and most preferably mammalian host cells, is the most typical because such eukaryotic cells, and in particular mammalian cells, are more likely than prokaryotic cells to assemble and secrete a properly folded and immunologically active antibody or antigen binding region.

Expression vectors include plasmids, retroviruses, cosmids, YACs (yeast artificial chromosomes), EBV (Epstein-Barr virus) derived episomes, and the like. A convenient vector is one that encodes a functionally complete human CH (constant heavy) or CL (constant light) immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions.

The expression vector and expression control sequences are chosen to be compatible with the expression host cell used. The antibody variable heavy chain nucleic acid and the antibody variable light chain nucleic acids of the present invention can be inserted into separate vectors or, frequently, both genes are inserted into the same expression vector. The nucleic acids can be inserted into the expression vector by standard methods (e.g., ligation of complementary restriction sites on the antibody nucleic acid fragment and vector, or blunt end ligation if no restriction sites are present). The heavy and light chain variable regions of antibodies can be used to create full-length antibody genes of any antibody isotype by inserting them into expression vectors already encoding heavy chain constant and light chain constant regions of the desired isotype (and subclass) such that the VH segment is operatively linked to the CH segment(s) within the vector and the VL segment is operatively linked to the CL segment within the vector. Additionally or alternatively, the expression vector can encode a signal peptide that facilitates secretion of the antibody or antigen binding region chain from a host cell. The antibody or antigen binding region chain gene can be cloned into the vector such that the signal peptide is linked in-frame to the amino terminus of the antibody/antigen binding region chain gene. The signal peptide can be an immunoglobulin signal peptide or a heterologous signal peptide (i.e., a signal peptide from a non-immunoglobulin protein).

In addition to the CDR (complementarity determining region) comprising sequence, the expression vectors of the invention carry regulatory sequences that control the expression of the sequence in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, and the like. Exemplary regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or beta-globin promoter.

In addition to the antibody or antigen binding region nucleic acids and regulatory sequences, the expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Exemplary selectable marker genes include the dihydrofolate reductase (DHFR) gene (for use in dhfr-host cells with methotrexate selection/amplification) and the neo gene (for G418 selection).

Preferred mammalian host cells for expressing the recombinant antibodies or antigen binding regions of the invention include Chinese Hamster Ovary (CHO cells) (including dhfr-CHO cells, described in Urlaub and Chasin, (1980) Proc. Natl. Acad. Sci. USA 77:4216-4220, used with a DHFR (dihydrofolate reductase) selectable marker, e.g., as described in R. J. Kaufman and P. A. Sharp (1982) Mol. Biol. 159:601-621), NS/0 myeloma cells, COS cells and SP2.0 cells. In particular for use with NS/0 myeloma cells, another preferred expression system is the GS gene expression system disclosed in WO 87/04462, WO 89/01036 and EP 338 841. When expression vectors of the invention are introduced into mammalian host cells, the antibodies or antigen binding regions are produced by culturing the host cells for a period of time sufficient to allow for expression of the antibody or antigen binding region in the host cells or, more preferably, secretion of the antibody or antigen binding region into the culture medium in which the host cells are grown.

Once expressed, antibodies and antigen binding regions of the invention can be purified according to standard methods in the art, including HPLC purification, fraction column chromatography, gel electrophoresis and the like (see, e.g., Scopes, Protein Purification, Springer-Verlag, NY, 1982). In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxylapatite chromatography; isoelectric focusing; polyacrylamide gel electrophoresis; and combinations of such and other techniques. In certain embodiments, a polypeptide is purified by fast protein liquid chromatography or by high pressure liquid chromotography (HPLC).

Multispecific molecules of the present invention can be made using chemical techniques (see e.g., D. M. Kranz et al., Proc. Natl. Acad. Sci. USA 78:5807 (1981), "polydoma" techniques (See U.S. Pat. No. 4,474,893, to Reading), or recombinant DNA techniques. In particular, multispecific molecules of the present invention can be prepared by conjugating the constituent binding specificities. For example, each binding specificity of the multispecific molecule can be generated separately and then conjugated to one another. A variety of coupling or cross-linking agents can be used for covalent conjugation of peptides. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.). A "linker" group is optional constituent of a binding polypeptide. When present, its chemical structure is not critical, since it serves primarily as a spacer. The linker can be made up of amino acids linked together by peptide bonds. Thus, in some embodiments, the linker is made up of from 1 to 20 amino acids linked by peptide bonds, wherein the amino acids are selected from the 20 naturally occurring amino acids. One or more of these amino acids may be glycosylated, as is well understood by those in the art. Alternatively, both binding specificities can be encoded in the same vector and expressed and assembled in the same host cell. Methods for preparing bi- and multi-specific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Therapeutically Effective Dose of VEGFR Inhibitor and Ang2 Inhibitor

The present invention includes a method to treat a human RCC patient with a therapeutically effective amount of a VEGFR inhibitor and an Ang2 inhibitor so as to inhibit, halt, reverse progression of the tumor, or otherwise result in a statistically significant increase in progression-free survival (i.e., the length of time during and after treatment in which a patient is living with renal cancer that does not get worse), or overall survival (also called "survival rate"; i.e., the percentage of people in a study or treatment group who are alive for a certain period of time after they were diagnosed with or treated for RCC) relative to treatment with a control.

In the method of the present invention, a therapeutically effective amount of the Ang2 inhibitor can be administered in combination with a VEGFR inhibitor to those RCC patients who would derive clinical benefit from such administration as determined by the predictive method of the invention. The therapeutically effective dose of the specific binding agent can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The specific binding agent is administered at doses and rates readily determined by those of ordinary skill in the art. In some embodiments, the specific binding agent is an antibody or peptibody administered intravenously once a week. In some embodiments, the taxane is administered once a week (e.g., intravenously) for three weeks and is not administered the fourth week of a four week cycle. In some embodiments, the Ang2 inhibitor of the present invention is administered to the patient at a dose ranging from 0.3 to 30 mg/kg of patient body weight, often at from 1 to 20 mg/kg, or 3 to 15 mg/kg. In certain embodiments the VEGFR inhibitor (e.g., sorafenib, fluoro-sorafenib) is administered once a week at approximately 40 to 120 mg/m$^2$ (square meter of patient surface area), often at between 50 to 80 mg/m2, and in some specific embodiments at around 80 mg/m2. In other embodiments, when administered once every three weeks, the dose of taxane ranges from between 50 to 225 mg/m2, often at 135 to 200 mg/m2. Conveniently, the dose of Ang2 inhibitor of the present invention is calculated using the standard pharmacokinetic parameter AUC (area under curve) wherein the dosage range is 5-40 mg-hr/ml, often at 6 to 25 mg-hr/ml. In some embodiments, the dose in milligrams of peptibody AMG 386 (2XCon4(C)) to be administered is calculated per the formula 530+(5.0*Baseline Creatinine Clearance [in mL/min]), wherein baseline creatinine clearance (CrCL) is to be determined by the Cockcroft and Gault equation (*Nephron* 1976 16: 31-41). Thus, when the CrCL is between 40 to 70 the calculated dose is 840 mg of 2XCon4(C), when the CrCL is 70 to 90 the calculated dose is 960 mg, when the CrCL is 90 to 110 the calculated dose is 1080 mg, when the CrCL is 110 to 140 the calculated dose is 1200 mg, when the CrCL is 140 to 160 the calculated dose is 1320 mg, when the CrCL is 160 to 190 the calculated dose is 1440 mg, when the CrCL is 190 to 200 the calculated dose is 1560 mg of 2XCon4(C). In some embodiments, the dosage of AMG 386 is (in milligrams/kilogram of bodyweight): 10 mg/kg, 15 mg/kg, 20 mg/kg, 25 mg/kg, or 30 mg/kg.

The VEGFR inhibitor of the present invention can be administered prior to and/or subsequent to (collectively, "sequential treatment"), and/or simultaneously with ("concurrent treatment") a specific binding agent of the present invention. Sequential treatment (such as pretreatment, post-treatment, or overlapping treatment) of the combination, also includes regimens in which the drugs are alternated, or wherein one component is administered long-term and the other(s) are administered intermittently. Components of the combination may be administered in the same or in separate compositions, and by the same or different routes of administration. Methods and dosing of administering chemotherapeutic agents are known in the art. Standard dosages and methods of administrations can be used, for example per the Food and Drug Administration (FDA) label. The VEGFR inhibitor of the present invention may be given as a drip (infusion) through a cannula inserted into a vein (IV), through a central line, which is inserted under the skin into a vein near the collarbone, or a peripherally inserted central catheter (PICC) line. The dose of VEGFR inhibitor is often administered in a fixed-time such as 30 minutes. Alternatively, the dose can be administered at a fixed rate (e.g., 10 mg/m$^2$/minute).

Pharmaceutical Formulation and Administration

The pharmaceutical composition comprising the Ang2 inhibitor of the present invention may contain formulation materials for modifying, maintaining or preserving, for example, the pH, osmolarity, viscosity, clarity, color, isotonicity, odor, sterility, stability, rate of dissolution or release, adsorption, or penetration of the composition.

The primary vehicle or carrier in a pharmaceutical composition may be either aqueous or non-aqueous in nature. For example, a suitable vehicle or carrier may be water for injection or physiological saline, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilate using appropriate excipients such as sucrose.

The formulation components are present in concentrations that are acceptable to the site of administration. For example, buffers are used to maintain the composition at physiological pH or at slightly lower pH, typically within a pH range of from about 5 to about 8. A particularly suitable vehicle for parenteral administration is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provide for the controlled or sustained release of the product which may then be delivered via a depot injection.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration. In a specific embodiment, a lyophilized peptibody, such as 2XCon4(C), is formulated as disclosed in WO 2007/124090 (incorporated herein by reference).

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The above listings are by way of example only, and do not preclude the use of other compounds or treatments which can be used concurrently with the compounds described herein that are known by those skilled in the art or that could be arrived at by those skilled in the art using the guidelines set forth in this specification.

The invention will now be further described with reference to the following non-limiting examples.

EXAMPLE 1

This example describes a phase 2, randomized, double-blind, placebo controlled, multi-center study to estimate the improvement in progression free survival (PFS) and evaluate the safety and tolerability of AMG 386 in combination with sorafenib in the treatment of subjects with advanced clear cell carcinoma of the kidney. A more complete description of the study design is disclosed at clinicaltrials.gov, the disclosure of which is incorporated herein by reference.

The number of patients to be enrolled was approximately 150. Patients eligible for the study were at least 18 years of age. Both genders were eligible although no healthy patients were eligible. The primary outcome measured was PFS while the secondary outcome included objective response rate, duration of response, and change in continuous measures of tumor burden.

| ARMS | ASSIGNED INTERVENTIONS |
|---|---|
| ARM A: Experimental Interventions: Drug: AMG 386 Drug: Sorafenib | Drug: AMG 386 10 mg/kg IV (intravenous) weekly until unacceptable toxicity or disease progression Drug: Sorafenib 400 mg PO (orally) BID (twice a day) |
| ARM B: Experimental Interventions: Drug: AMG 386 Drug: Sorafenib | Drug: AMG 386 3 mg/kg IV weekly until unacceptable toxicity or disease progression Drug: Sorafenib 400 mg PO BID |
| ARM C: Active Comparator Intervention: Drug: Sorafenib | Drug: Sorafenib 400 mg PO BID |

Inclusion Criteria were as follows:
1) Subjects must have a histologically confirmed metastatic RCC with a clear cell component.
2) Low or intermediate risk according to the Memorial Sloan Kettering Cancer Center (MSKCC) prognostic risk classification.
3) Measurable disease with at least one unidimensionally measurable lesion per RECIST guidelines with modifications.
4) Adequate organ and hematological function as evidenced by laboratory studies conducted at screening.
5) ECOG (Eastern Cooperative Oncology Group) performance status of 0 or 1.

Exclusion Criteria were as follows:
Disease Related
1) Known history of central nervous system metastases.
2) Previous treatment (excluding surgery and palliative radiotherapy) for advanced or metastatic renal cell carcinoma.
3) Focal radiation therapy for palliation of pain from bony metastases within 14 days of randomization.

Medications
1) Currently or previously treated with inhibitors of VEGF.
2) Currently or previously treated with inhibitors of angiopoietin or Tie2.
3) Currently or previously treated with bevacizumab.

General Medical
1) Diagnosis of acute pancreatitis.
2) Myocardial infarction, cerebrovascular accident, transient ischemic attack, percutaneous transluminal coronary angioplasty/stent, congestive heart failure, grade 2 or greater peripheral vascular disease, arrhythmias not controlled by outpatient medication, or unstable angina within 1 year prior to randomization.
3) Major surgery within 30 days before randomization or still recovering from prior surgery.
4) Uncontrolled hypertension as defined as diastolic>90 mmHg OR systolic>150 mmHg. Anti-hypertensive medications are permitted.

Other
1) Other investigational procedures are excluded.
2) Subject currently is enrolled in or has not yet completed at least 30 days since ending other investigational device or drug study(s), or subject is receiving other investigational agent(s).

EXAMPLE 2

This example describes an analysis of the relationship between patient PLGF concentration and PFS (progression free survival) of patients enrolled in the phase 2 study described in Example 1.

Renal cancer patient's circulating levels of protein placental growth factor (PLGF) was analyzed along with a number of other analytes to determine if it was predictive of how well they will respond after treatment with AMG 386 and sorafenib. In a clinical trial (Example 1), patients with renal cancer were treated with 400 mg BID (twice a day) sorafenib and either 10 mg/kg QW (once a week) AMG 386, 3 mg/kg QW AMG 386, or placebo AMG 386. Serum samples were collected prior to treatment (baseline) and used to measure circulating levels of the protein PLGF. The baseline patient PLGF concentration was analyzed to determine if it was informative of how well the patient would respond to the treatment regimens.

The patients PLGF concentrations were determined and tested for statistical association with progression free survival (PFS) time. Patient PLGF concentrations were found to be predictive of response to the combination therapy of AMG 386 and sorafenib ($p=0.017$), when patients were classified as to whether their baseline PLGF was "high" (above the median PLGF concentration parameter) or "low" (below the median PLGF concentration parameter). Patient classification was based on dichotomization by the overall median baseline PLGF (median PLGF concentration parameter). Predictive significance was determined with a Cox proportional hazards model of PFS with the factors PLGF, cohort, and the interaction between PLGF and cohort. If the interaction factor had a p-value<0.05 then patient PLGF concentration was considered to be predictive of PFS.

Figure 4:
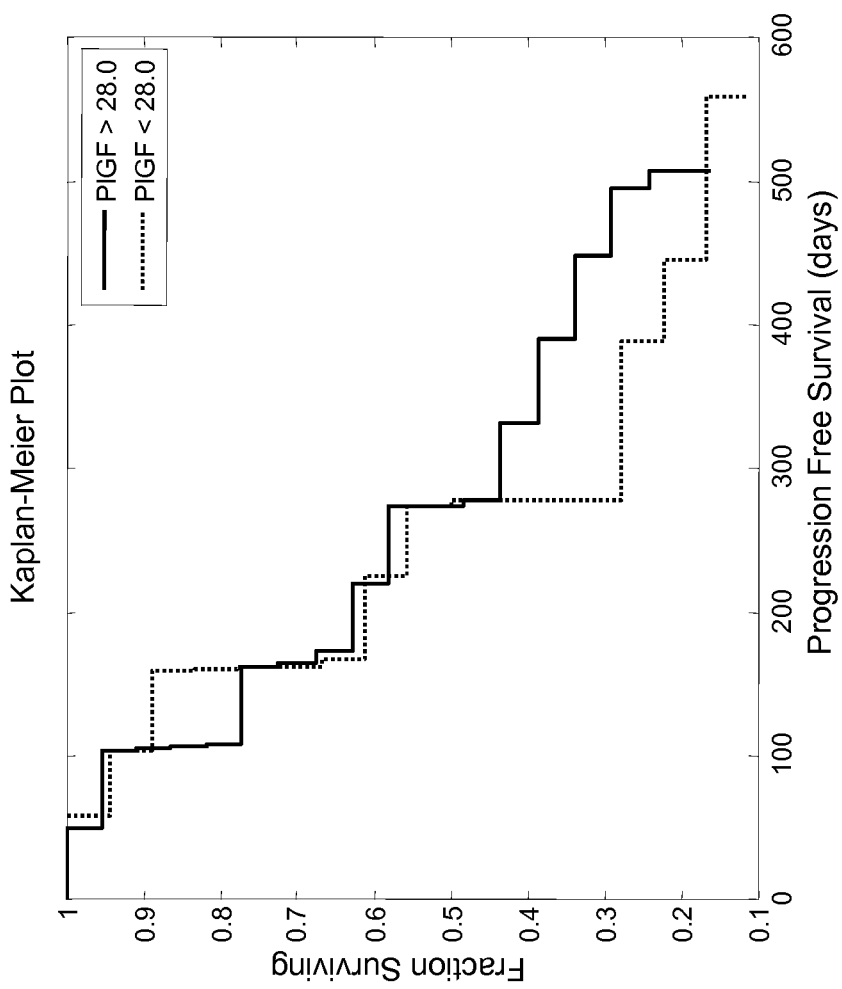

The relationship between PLGF and survival is illustrated graphically with Kaplan-Meier (KM) plots (FIGS. 1-4). Each curve in a KM plot shows how the fraction of patients having PFS changes with time after the start of treatment. Differences between survival curves are evaluated with the Cox proportional hazards test. When all patients, regardless of treatment, were classified into PLGF high and low groups, those with low baseline patient PLGF concentration had longer PFS (FIG. 1, hazard ratio=1.92, $p=0.00217$). A difference in PFS based on PLGF level was not seen in the patients that only received only the VEGF receptor inhibitor sorafenib (FIG. 4, hazard ratio=0.83, $p=0.59$). In contrast, a significant difference was seen in both of the AMG 386 treated cohorts (FIGS. 2 and 3, hazard ratio=2.76 & 3.51, respectively, $p<0.01$).

The observation of a significant association between patient PLGF concentration and survival in the AMG 386 treated patients and no association in the patients treated with sorafenib alone indicates that baseline PLGF is predictive of response to AMG 386 vs. placebo. Renal cancer patients with low patient PLGF concentrations are predicted to survive longer than those with high patient PLGF concentrations when they are treated with AMG 386 in combination with sorafenib versus treatment with sorafenib alone.

We claim:
1. A method of treating a patient with renal cell carcinoma (RCC) with a therapeutically effective amount of a vascular endothelial growth factor (VEGFR) inhibitor and an angiopoietin 2 (Ang2) inhibitor, the method comprising:
 measuring the concentration of placental growth factor (PLGF) in an RCC patient sample:

determining that the PLGF concentration in said patient sample is lower than a PLGF concentration parameter; and administering a therapeutically effective amount of a VEGFR inhibitor and an Ang2 inhibitor to said patient.

2. A method of treating a patient with renal cell carcinoma (RCC) with a therapeutically effective amount of a vascular endothelial growth factor (VEGFR) inhibitor and an angiopoietin 2 (Ang2) inhibitor, the method comprising;

measuring the serum concentration of placental growth factor (PLGF) in an RCC patient sample;

determining that the serum PLGF concentration in said patient sample is lower than 40 pg/mL; and administering a therapeutically effective amount of a VEGFR inhibitor and an Ang2 inhibitor to said patient.

3. The method of claim 1, wherein the Ang2 inhibitor is AMG 386 and the VEGFR inhibitor is sorafenib or fluorosorafenib.

4. The method of claim 1, wherein the Ang2 inhibitor is H41.4 and the VEGFR inhibitor is sorafenib or fluorosorafenib.

5. The method of claim 1, wherein the Ang2 inhibitor is at least one of CVX-060, MEDI3617, DX-2240, REGN910, AZD-5180, CGI-1842, LC06, CGEN-25017, RG7594, CVX-241 or TAvi6.

6. The method of claim 1, wherein the PLGF concentration parameter is a serum PLGF concentration between 22 pg/mL and 40 pg/mL, inclusive.

7. The method of claim 1, wherein the PLGF concentration parameter is a serum PLGF concentration of 28 pg/ml.

8. The method of claim 1, wherein the PLGF concentration parameter is within one standard deviation of the mean serum PLGF concentration.

9. The method of claim 8, wherein the serum PLGF concentration parameter is the mean serum PLGF concentration parameter.

10. The method of claim 1 or 2, wherein the VEGFR inhibitor is sorafenib.

11. The method of claim 1 or 2, wherein the VEGFR, inhibitor and the Ang2 inhibitor are administered concurrently.

12. The Method of claim 1, wherein the Ang2 inhibitor is also an Ang1 inhibitor.

13. The method of claim 1, wherein the Ang2 inhibitor is a binding polypeptide.

14. The method of claim 13, wherein the binding polypeptide is an anti-Ang2 antibody.

15. The method of claim 13, wherein the Ang2 inhibitor is an anti-Tie2 antibody.

16. The method of claim 13, wherein the bispecific binding polypeptide is an anti-VEGFR and anti-Ang2 bispecific binding polypeptide.

17. The method of claim 13, wherein the bispecific binding polypeptide is an anti-DLL4 and anti-Ang2 bispecific binding polypeptide.

18. The method of claim 13, wherein the binding polypeptide is a soluble Tie2-Fc polypeptide.

19. The method according to claim 2, wherein the serum PLGF concentration is lower than 32 pg/mL.

20. The method according to claim 2, wherein the serum PLGF concentration is lower than 28 pg/mL.

21. A method of treating a patient with renal cell carcinoma (RCC) with a therapeutically effective amount of AMG 386 and sorafenib, the method comprising:

measuring the serum concentration of placental growth factor (PLGF) in an RCC patient sample;

determining that the serum PLGF concentration in said patient sample is lower than 32 pg/mL; and administering a therapeutically effective amount of amount of AMG 386 and sorafenib to said patient.

22. The method according to claim 21, wherein the method comprises determining that the serum PLGF concentration in said patient sample is lower than 28 pg/mL.

* * * * *